United States Patent
Cheng et al.

(10) Patent No.: US 11,246,643 B2
(45) Date of Patent: Feb. 15, 2022

(54) MEDICAL SYSTEM WITH OPTIMIZED EFFECTS

(71) Applicant: Gyrus ACMI, Inc., Southborough, MA (US)

(72) Inventors: Ming J. Cheng, West Warwick, RI (US); David C. Church, Millington, TN (US)

(73) Assignee: Gyrus Acmi, Inc., Westborough, MA (US)

( * ) Notice: Subject to any disclaimer, the term of this patent is extended or adjusted under 35 U.S.C. 154(b) by 0 days.

(21) Appl. No.: 15/906,137

(22) Filed: Feb. 27, 2018

(65) Prior Publication Data

US 2019/0262061 A1    Aug. 29, 2019

(51) Int. Cl.
*A61B 18/14*    (2006.01)
*A61B 18/12*    (2006.01)
*A61B 18/00*    (2006.01)

(52) U.S. Cl.
CPC .......... *A61B 18/14* (2013.01); *A61B 18/1206* (2013.01); *A61B 18/1402* (2013.01); *A61B 2018/00029* (2013.01); *A61B 2018/00327* (2013.01); *A61B 2018/00577* (2013.01); *A61B 2018/00601* (2013.01); *A61B 2018/00642* (2013.01); *A61B 2018/00684* (2013.01); *A61B 2018/00744* (2013.01); *A61B 2018/00791* (2013.01); *A61B 2018/00827* (2013.01); *A61B 2018/00863* (2013.01); *A61B 2018/00875* (2013.01); *A61B 2018/00892* (2013.01); *A61B 2018/00982* (2013.01); *A61B 2018/126* (2013.01); *A61B 2018/1253* (2013.01); *A61B 2018/1412* (2013.01); *A61B 2218/002* (2013.01)

(58) Field of Classification Search
CPC ........... A61B 2018/00011; A61B 2018/00642; A61B 2018/00714; A61B 2018/00744; A61B 2018/00791; A61B 2018/00797; A61B 2018/1472
See application file for complete search history.

(56) References Cited

U.S. PATENT DOCUMENTS

| | | | | |
|---|---|---|---|---|
| 5,342,357 A * | 8/1994 | Nardella | ............ | A61B 18/1206 606/38 |
| 5,728,094 A * | 3/1998 | Edwards | ................ | A61B 17/24 606/41 |
| 6,139,571 A * | 10/2000 | Fuller | ........................ | A61F 7/12 604/113 |
| 7,083,601 B1* | 8/2006 | Cosmescu | .............. | A61B 18/14 601/35 |
| 8,690,870 B2* | 4/2014 | Wang | ................. | A61B 18/1492 606/41 |

(Continued)

*Primary Examiner* — Ronald Hupczey, Jr.
(74) *Attorney, Agent, or Firm* — Schwegman Lundberg & Woessner, P.A.

(57) ABSTRACT

Provided is a medical system comprising a medical device, a feature sensor and a logic controller or processor wherein the logic controller is configured to monitor or control an operation of the medical device in response to the input of the feature sensor. Also provided is a method of monitoring or controlling an operation of a medical device by a logic controller through a plurality of sensors. Further provided is a method of minimizing or preventing tissue sticking of an electrosurgical device during a medical procedure on a patient.

14 Claims, 7 Drawing Sheets

(56) References Cited

U.S. PATENT DOCUMENTS

| | | | |
|---|---|---|---|
| 8,979,840 B2* | 3/2015 | Christian | A61B 18/1492 606/41 |
| 2012/0165812 A1* | 6/2012 | Christian | A61B 18/1492 606/41 |
| 2012/0232544 A1* | 9/2012 | Willyard | A61B 18/1815 606/33 |
| 2013/0310823 A1* | 11/2013 | Gelfand | A61B 18/1492 606/33 |

* cited by examiner

MEDICAL SYSTEM WITH OPTIMIZED EFFECTS

FIELD

The present disclosure relates generally to a medical system for monitoring and controlling an operation of a medical device. More particularly, the present disclosure relates to a medical system configured to optimize certain operational parameters or features of an electrosurgical device during its use in electrosurgery.

BACKGROUND

A variety of electrosurgical instruments include a tissue cutting element and one or more elements that transmit radiofrequency energy to tissue to coagulate or seal the tissue. These electrosurgical instruments may often face the challenge of blood and tissue sticking while performing electrosurgical operations. Once the sticking builds up, it will significantly affect the effectiveness of the electrosurgical operations of these electrosurgical instruments.

Accordingly, there is an ongoing need for improved devices and methods for more efficient electrosurgical operations.

SUMMARY

In one embodiment, the present disclosure provides a medical system comprising a medical device and a logic controller or processor configured to monitor or control one or more parameters or features of the medical device during a medical operation.

In one embodiment, the present disclosure provides a medical system comprising an electrosurgical device having a surgical electrode, a feature sensor, and a logic controller or processor wherein the logic controller is configured to monitor or control one or more parameters or features of the electrosurgical device in response to an input from the feature sensor.

In one embodiment, the present disclosure provides a medical system comprising an electrosurgical device having a surgical electrode and an irrigation line, an irrigation flow sensor, a feature sensor, and a logic controller or processor wherein the logic controller is configured to monitor or control the flow rate of an irrigation fluid of the irrigation line through its closed-loop communication with the irrigation flow sensor, the feature sensor, and the electrosurgical device.

In one embodiment, the present disclosure also provides a method of monitoring or controlling one or more operational parameters or features of a medical device through a logic controller or processor. The method includes providing a medical system comprising the medical device and the logic controller or processor.

In one embodiment, the present disclosure further provides a method of improving or optimizing the operational efficiency or outcome of an electrosurgical device. The method includes providing the electrosurgical device having a surgical electrode and an irrigation line. The method also includes positioning the electrosurgical device properly at a treatment site. The method further includes turning on the electrosurgical device and supplying an irrigation fluid to the electrosurgical device. The method also includes adjusting the irrigation fluid to a certain flow rate to improve or optimize the operational efficiency or outcome of the electrosurgical device.

In one embodiment, the present disclosure also provides a method of minimizing or preventing tissue or blood sticking of an electrosurgical device, the method including providing a medical system comprising the electrosurgical device and a logic controller or processor configured to monitor or control one or more operational parameters or features of the electrosurgical device to minimize or prevent tissue or blood sticking.

In one embodiment, the present disclosure also provides a method of minimizing or preventing tissue sticking on a surgical electrode of an electrosurgical device during a medical procedure on a patient. The method comprises: providing the electrosurgical device having the surgical electrode and an irrigation line; supplying an irrigation fluid through the irrigation line once the electrosurgical device is power on; and adjusting the irrigation fluid to a certain flow rate to minimize or prevent tissue sticking on the surgical electrode of the electrosurgical device.

DETAILED DESCRIPTION

Figure 1:
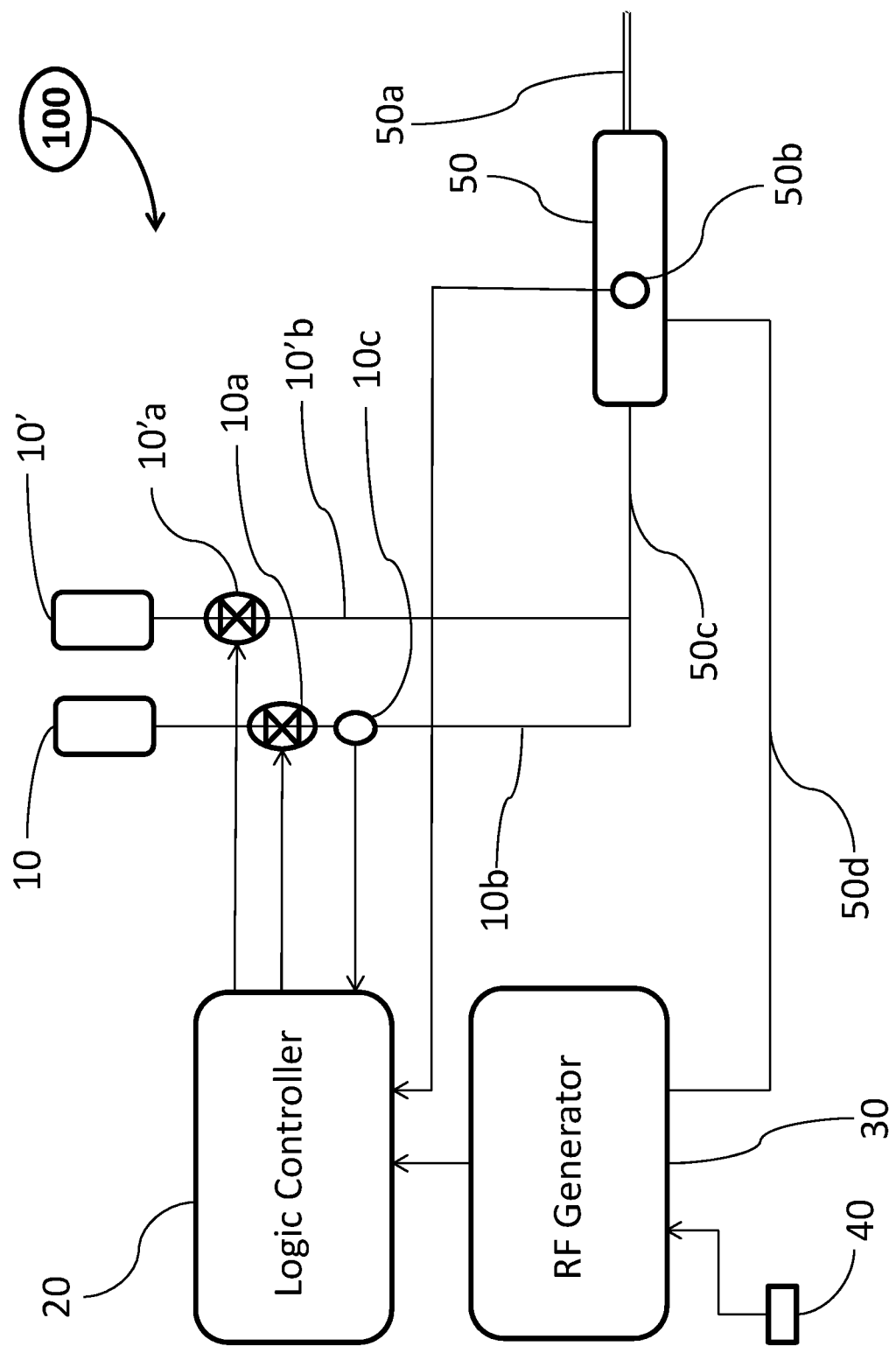
FIG. 1 is a block diagram of an electrosurgical system in accordance with one aspect of the present disclosure.

The explanations and illustrations presented herein are intended to acquaint others skilled in the art with the disclosure, its principles, and its practical applications. Those skilled in the art may adapt and apply the disclosure in numerous forms, as may be best suited to the requirements of a particular use. The specific embodiments of the present disclosure as set forth are not intended to be exhaustive or limiting of the invention. The scope of the invention should be determined not with reference to the above description, but should be determined with reference to the appended claims, along with the full scope of equivalents to which such claims are entitled.

The terms "one embodiment", "an embodiment", "another embodiment", "some embodiments", "other embodiments", and similar expressions indicate that the embodiment or embodiments described may include a particular feature, structure, or characteristic, but every embodiment may not necessarily include the particular feature, structure, or characteristic. Moreover, such phrases are not necessarily referring to the same embodiment. Furthermore, when a particular feature, structure, or characteristic is described in connection with an embodiment, it would be within the knowledge of one skilled in the art to incorporate such feature, structure, or characteristic into other embodiments, whether or not explicitly described, unless clearly stated to the contrary. That is, the various individual elements described below, even if not explicitly shown in a particular combination, are nevertheless contemplated as being combinable with each other to form other additional embodiments or to complement and/or enrich the described embodiment or embodiments, as would be understood by one of ordinary skill in the art.

The articles "a", "an" and "the" are used herein to refer to one or to more than one (i.e. to at least one) of the grammatical object of the article unless otherwise clearly indicated by contrast. By way of example, "an element" means one element or more than one element.

The term "including" is used herein to mean, and is used interchangeably with, the phrase "including but not limited to". The term "or" is used herein to mean, and is used interchangeably with, the term "and/or", unless context clearly indicates otherwise.

The term "such as" is used herein to mean, and is used interchangeably, with the phrase "such as but not limited to". Unless specifically stated or obvious from context, as used herein, the term "about" is understood as within a range of normal acceptance in the art, for example within standard deviations of the mean.

The term "proximal" is herein used to mean a position or direction closest to a user of the device and is in a position or direction opposite to the term "distal".

The term "distal" is herein used to mean a position or direction furthest away from a user of the device and is a position or direction opposite to the term "proximal".

As used herein, the term "subject" can refer to any warm-blooded organism including, but not limited to, human beings, pigs, rats, mice, dogs, goats, sheep, horses, monkeys, apes, rabbits, cattle, etc.

All numeric values are herein assumed to be modified by the term "about" whether or not explicitly indicated. The term "about", in the context of numeric values, generally refers to a range of numbers that one of skill in the art would consider equivalent to the recited value (i.e., having the same function or result). In many instances, the term "about" may include numbers that are rounded to the nearest significant figure. Other uses of the term "about" (i.e., in a context other than numeric values) may be assumed to have their ordinary and customary definition(s), as understood from and consistent with the context of the specification, unless otherwise specified. Even more specifically, "about" can be understood as within 10%, 9%, 8%, 7%, 6%, 5%, 4%, 3%, 2%, 1%, 0.5%, 0.1%, 0.05%, or 0.01% of the stated value. Unless otherwise stated, all ranges include both endpoints and all numbers between the endpoints. The use of "about" or "approximately" in connection with a range applies to both ends of the range. Thus, "about 10 to 30" is intended to cover "about 10 to about 30", inclusive of at least the specified endpoints.

In one embodiment, the present disclosure provides a medical system comprising a medical device and a logic controller or processor configured to monitor or control one or more parameters or features of the medical device. In one embodiment, the medical system also comprises a RF generator. In one embodiment, the medical system further comprises a power switch of the RF generator. In one embodiment, the power switch is in the form of a footswitch or a push button. In one embodiment, the medical system further comprises a regular irrigation assembly. In one embodiment, the medical system further includes a low flow irrigation assembly. In one embodiment, the medical system further comprises one or more flow sensors. In one embodiment, the medical system further comprises one or more feature sensors or indicators or recorders.

In one embodiment, the present disclosure provides a medical system comprising a medical device, a RF generator, a regular irrigation assembly, a low flow irrigation assembly and a logic controller or processor configured to monitor or control one or more parameters or features of the medical device. In one embodiment, the regular irrigation assembly comprises a fluid container or storage device, a fluid pump and one or more valves. In one embodiment, the flow rate of the regular irrigation assembly may be configured to be controllable by the logic controller or processor. In one embodiment, the flow rate of the regular irrigation assembly may be configured to have one fixed rate whenever the regular irrigation flow is on. In one embodiment, the flow rate of the regular irrigation assembly may be configured to be adjustable or variable. In one optional embodiment, the flow rate of the regular irrigation assembly may be configured to be feedback controlled by the logic controller in response to an input from a feature sensor or indicator configured to be in communication with the medical device. In one embodiment, the feature sensor is a temperature sensor. In one embodiment, the flow rate is feedback controlled by the input of a feature sensor. In one embodiment, the low flow irrigation assembly comprises a fluid container or storage device, a fluid pump, one or more valves, and a flow rate sensor. The logic controller or processor is configured to determine whether the liquid pump of the low flow irrigation assembly should be turned on or off based on the input from one or more feature sensors or indicators that are in electrical or electromagnetic communication with the medical device. When the logic controller receives from the one or more feature sensors or indicators the data that are beyond or below the pre-established values, the logic controller will instruct the medical system to turn off the regular irrigation assembly, and concurrently turn on the low flow Irrigation assembly for low flow irrigation. In one embodiment, the regular irrigation assembly and the low flow irrigation assembly may share the same fluid container. In one embodiment, the regular irrigation assembly and the low flow irrigation assembly may have different fluid containers. In one embodiment, the irrigation fluid may be saline. In one embodiment, the regular irrigation fluid pump and the low flow irrigation fluid pump may be peristaltic pump.

In one embodiment, the present disclosure provides a medical system comprising a medical device, a RF generator, a combined irrigation assembly, and a logic controller or processor configured to monitor or control one or more parameters or features of the medical device. The combined irrigation assembly comprises a fluid container or storage device, a fluid pump and one or more valves, and a flow sensor. The combined irrigation assembly is configured to function as a regular irrigation assembly and as a low flow irrigation assembly as well. The logic controller or processor is configured to determine the flow rate of the combined irrigation assembly in response to the input from one or more feature sensors or indicators that are in electrical or electromagnetic communication with the medical device. Under normal working conditions, the combined irrigation assembly functions as regular irrigation assembly until or unless the logic controller receives an input from the feature sensor to instruct or demand a switch into low flow irrigation flow.

In the above embodiments, the medical device comprises a handpiece, a RF element, an irrigation line and a suction line. The RF element may be a monopolar RF element or a bipolar RF element. The RF element may be monopolar electrode or bipolar electrodes.

In the above embodiments, the medical device may be an electrosurgical device. In the above embodiments, the medical device may be an electrosurgical cutting device. It may be an electrosurgical coagulation device. It may be a radiofrequency (RF) electrosurgical device. The RF electrosurgical device may have a surgical or RF electrode. The surgical or RF electrode may be operated in either bipolar or monopolar mode with a ground pad electrode. In a monopolar mode of delivering RF energy, a single electrode is used in combination with an indifferent electrode patch that is applied to the body to form the other contact and complete an electrical circuit. Bipolar operation is made possible when two or more electrodes are used. Multiple electrodes may also be used in bipolar operations.

In the above embodiments, the RF generator may be for monopolar electrosurgery or for bipolar electrosurgery. With monopolar electrosurgery, a patient forms a major part of the electrical circuit. An active cable from the electrosurgery unit carries current to the active monopolar electrode. Current then spreads through the tissue to be collected and returned to the electrosurgery unit by a 'patient plate electrode' attached to the patient. There are no intended thermal tissue effects at the plate electrode, since the current is less concentrated (The patient plate electrode is also known as dispersive, neutral, passive or return electrode). Unlike monopolar electrosurgery where a patient's body forms a major part of the electrical circuit, with bipolar electrosurgery only the tissue grasped between the tips of a pair of bipolar elements forms part of the electrical circuit. These bipolar elements incorporate two active electrodes, which also return the current, the same as a patient plate electrode in monopolar electrosurgery. Both electrodes are isolated in respect of earth and are routed directly to the site of the operation. Bipolar electrosurgery typically uses a frequency between 250 kHz and 1 MHz. When using bipolar electrosurgery, the active electrodes delivering power to the surgical site, can either be hand or foot activated.

In the above embodiments, the logic controller or processor may be a microprocessor, an application specific integrated circuit (ASIC) state machine, a gate array, and the like so long as it can perform the desired functions and activities as described herein. More particularly, the logic controller should be able to receive inputs from the sensors, switches, and similar devices of the medical system. Some of the basic components of the logic controller are input modules, a central processing unit, output modules, and a programming device. When an input is activated, some output will also be activated by whatever the system is told to do. In the above embodiments, the logic controller or processor may comprise more than one such controller as needed. In the above embodiments, the logic controller or processor may have a user input and a display panel. The user input may allow the user to input different parameters or values as desired.

In the above embodiments, the logic controller or processor may be configured or programmed to be in communication with all the sensors including flow sensors and other feature sensors. The logic controller may be configured to be in communication with the regular irrigation assembly, the low flow irrigation assembly, and/or the combined irrigation assembly whenever necessary or desired. In the above embodiments, the logic controller may be configured to determine a condition of the medical system such as the power status of the RF generator and the power status of the regular irrigation assembly, the low flow irrigation assembly, and the combined irrigation assembly. In the above embodiments, the logic controller may be programmed to turn on or off the power of the RF generator and the power of the regular irrigation assembly, the low flow irrigation assembly, and the combined irrigation assembly. The logic controller may be configured to be located at a separate controlling system, or may be attachable to the medical device, or may be sized to be disposed on or inside the handpiece of the medical device.

In the above embodiments, the logic controller is programmed to receive data from the sensors, and process the received data to generate data, and subsequently compare the generated date with the pre-established/recorded data or with a look-up table, and then respond or make adjustments accordingly. The data received from the sensors may be recorded in the form of parameter or feature values. In some specific embodiments, the logic controller may be configured to determine the flow rate in response to a combination of outputs from the feature sensors or indicators. In some embodiments, the logic controller is programmed in a closed-loop manner in response to the data input from one or more irrigation flow sensors. In some embodiments, the logic controller may include a data collection phase and a comparison phase. During the data collection phase, the data from the sensors are recorded in the form of parameter values. The parameter values may describe or are indicative, of a condition of the medical device. The logic controller may be configured to make adjustments as needed. In some embodiments, the logic controller or processor may be configured to monitor the medical device for automatic operation.

In the above embodiments, the regular irrigation assembly may include one or more fluid pumps, one or more valves and one or more flow sensors, and other accessories. In the above embodiments, the low flow line may also include one or more fluid pumps, one or more valves and flow sensors, and other accessories. The regular irrigation assembly is configured to provide a regular irrigation low rate known in the art while the low flow irrigation assembly is configured to provide a low flow irrigation line when only a small amount of irrigation fluid is needed. One of the reasons for a separate low flow irrigation line is due to an easier operation and control of a low flow rate in comparison with using a regular irrigation line. The flow sensors may be disposed at any suitable position or place so long as they can properly function as intended.

In the above embodiments, the feature sensors or indicators may provide a variety of different functions, including but not limited to, initiation, programming, measuring, storing, analyzing, communicating, predicting, and displaying of a condition of the medical device. A wide variety of different feature sensors or indicators may be utilized, including but not limited to, temperature, electrical current, electrical voltage, bioimpedance, and the like. The temperature sensors may be IR temperature sensors, conventional sensors such as thermistors, thermocouples, resistive wires and the like. The feature sensors or indicators may have multiple features to enhance their sensing performance. The multiple features may enhance the medical system's ability to determine an optimal sensing situation. Size and shape of these feature sensors or indicators may also be optimized to maximize their sensing performance. Additionally, some feature sensors or indicators may be used for short term sensing, and others may be used for longer term sensing. More particularly, a temperature sensor sends back a temperature reading at a treatment site to the logic controller which then compares the reading with a set point temperature. The controller subsequently adjusts the irrigation flow in accordance with these calculations/comparisons. The temperature sensor may be at the tip of the surgical blade of the medical device or be just affixed to the medical device. It may also be placed in a place separate from the medical device.

In one embodiment, the present disclosure also provides a method of monitoring or controlling one or more parameters or features of a medical system, the method comprising providing a medical device and a logic controller or processor wherein the logic controller is configured to monitor and/or control the one or more parameters of the medical device in response to an input from a feature sensor configured to be in communication with the medical device. In one embodiment, the medical device has a surgical blade and an irrigation line. In one embodiment, the medical system has one or more feature sensors configured to measure or record one or more parameters or features of the medical device. In one embodiment, the one or more feature sensors may be an electrical current sensor, electrical voltage sensor, temperature sensor, or bioimpedance sensor. In one embodiment, the feature sensor is a temperature sensor. In one embodiment, the logic controller is configured to monitor and control flow rate of the irrigation line of the medical device in response to an input of a temperature sensor. In one embodiment, the irrigation flow rate may be adjusted to about 0.1 to 0.25 ml per second. In one embodiment, the operational temperature at the tip of the medical device may be manually adjusted to be about 80 to 99° C.

In one embodiment, the present disclosure further provides a method of monitoring or controlling the tissue or blood sticking of a medical device, the method including providing a medical system comprising the medical device and a logic controller or processor configured to monitor or control one or more parameters or features of the medical device. In one embodiment, the medical device has a surgical blade and an irrigation line. In one embodiment, the medical system has one or more feature sensors configured to measure or record one or more parameters or features of the medical device. In one embodiment, the feature sensor is a temperature sensor. In one embodiment, the logic controller is configured to monitor and control flow rate of the irrigation line of the medical device in response to an input of a temperature sensor. In one embodiment, the logic controller is configured to monitor and control the temperature range at the surgical blade of the medical device.

In one embodiment, the present disclosure also provides a method of minimizing or preventing tissue sticking on a surgical electrode of a medical device during a medical procedure on a patient, the method comprising: providing the medical device having the surgical electrode and an irrigation fluid line; supplying an irrigation fluid through the irrigation line once the medical device is power on to perform the medical procedure; and adjusting flow rate of the irrigation fluid to minimize or prevent tissue sticking on the surgical electrode of the medical device. In one embodiment, the method includes providing a logic controller configured to adjust the flow rate of the irrigation fluid in response to an input of a feature sensor configured to be in communication with the medical device. In one embodiment, the positioning step may be achieved through an endoscope. In one embodiment, the medical procedure is on a nasal cavity. In one embodiment, the medical procedure is a surgical operation for a nasal cavity.

In one embodiment, the present disclosure also provides a method of improving an operational efficiency or outcome of a medical device, the method comprising: providing the medical device having a surgical electrode and an irrigation fluid line; positioning the medical device properly at the treatment site; turning on the medical device; supplying an irrigation fluid to the medical device through the irrigation line; and adjusting flow rate of the irrigation fluid to improve the operational efficiency or outcome of the medical device.

In one embodiment, the method includes providing a logic controller configured to adjust the flow rate of the irrigation fluid in response to an input of a feature sensor configured to be in communication with the medical device. In one embodiment, the positioning step may be achieved through an endoscope. In one embodiment, the positioning step may be achieved through ultrasonic guidance.

In some embodiments, the method includes automatically monitor and control an operation of the medical device. The logic controller or processor may be configured to automatically generate at least some of the operational parameter values. The logic controller or processor may also be configured to compare and determine whether the generated parameter values are substantially similar to the pre-established or recorded values.

In the above embodiments, the surgical operation may be monitored based on a number of features or parameters or variations thereof including but not limited to, electrical current, electrical voltage, bioimpedance, temperature and the like. In one specific embodiment, the surgical operation is monitored for its temperature variations. The temperature variations may be monitored or recorded through a temperature sensor. The temperature sensor may be used in conjunction with other sensors. The medical system may be configured to automatically monitor and/or control each individual component of the system through the logic controller.

In the above embodiments, the method may include a data collection phase and a data comparison phase. During the data collection phase, the medical device is performing an operation to a subject, and generating various parameter or feature values. These feature or parameter values or variations thereof are then sent by the feature sensors or indicators or recorders to the logic controller for collection and recording. Subsequently, the logic controller is configured to compare these values with the pre-established or pre-recorded values or with a look-up table. The logic controller can then instruct the medical device to make any necessary adjustments/modifications in accordance with the calculations and/or comparisons. All the data collection and data comparison can be easily programmed into the logic controller in accordance with any specific needs of an electrosurgical operation.

In some embodiments, the method may involve manual intervention. More specifically, the medical system or device may be operated manually. There may need only one irrigation line if manual intervention is involved. In some embodiments, the irrigation flow rate may be manually adjusted. The flow rate may be manually operated and/or adjusted in response to observations realized or achieved through means known in the art such as endoscopy or ultrasonic imaging. In some embodiments, the irrigation flow rate may be manually adjusted to about 0.1 to 0.25 ml per second. In some embodiments, the operational temperature at the tip of the medical device may be manually adjusted. The temperature may be manually adjusted to be about 80 to 99° C. degree. In some embodiments, the surgical operation may be just for tissue coagulation or tissue sealing if the temperature is adjusted to be about 80 to 99° C. degree. In some embodiments, the medical device may be a bipolar coagulation device.

The principles of the present disclosure may be better understood with reference to the drawings and the accompanying descriptions, wherein like reference numerals have been used throughout to designate identical or similar elements. It should be understood that these drawings are not necessarily are drawn to scale. They are presented just for illustrative purposes only, and are not intended to limit the scope of the disclosure. Examples of materials, dimensions, and constructions are included for some elements. Those of ordinary skill in the art should understand that many of the examples provided have suitable alternatives and these alternatives should also be considered within the scope of this disclosure. Moreover, certain terminology is used herein for convenience only and is not to be taken as a limitation on the present disclosure.

FIG. 1 is a block diagram in accordance with one aspect of the present disclosure. The medical system 100 of FIG. 1 includes a medical device, a regular irrigation assembly, a low flow irrigation assembly, a logic controller or processor 20 (referred hereafter as logic controller for convenience), and a RF generator 30. More particularly, the medical device comprises a handpiece 50, a surgical blade assembly 50a, a feature sensor 50b, and an irrigation line 50c. Even though the feature sensor 50b is shown to be affixed onto the handpiece 50, it may be placed close to the tip of the blade assembly 50a, or may be disposed away from the handpiece 50 or even away from the medical device so long as it is configured to be in communication with the medical device. Moreover, the feature sensor 50b may comprise a plurality of different feature sensors even though only one is shown in FIG. 1. The medical system may also include a suction line to remove the irrigation fluid and other fluids or solids/debris even though it is not shown in FIG. 1.

The regular irrigation assembly comprises a regular irrigation container or storage device 10', a regular irrigation pump and valve block 10'a, and a regular irrigation flow line 10'b. The regular irrigation container 10' is used to store or hold an irrigation fluid. The irrigation fluid may be saline. The regular irrigation pump and valve block 10'a includes a fluid pump and at least a valve for controlling the flow of the irrigation fluid. The regular irrigation pump is used to transport the irrigation fluid from the irrigation container 10' to the medical device. The regular irrigation pump and the valve block 10'a may be built into one whole piece. However, it is preferable that they are physically separable. The fluid pump may be a peristaltic pump or other types of pumps. The pump and valve block 10'a may comprise one or more valves so long as it is configured to be capable of moderating or controlling the flow rate, pressure, and/or volume of the regular irrigation assembly line. The valve may be a pinch valve or other types of valves. The flow rate, pressure, and/or volume of the regular irrigation line may be manually controlled or adjusted. They may be automatically monitored and controlled by the logic controller 20 through the regular irrigation pump and valve block 10'a. They may also be feedback controlled by the logic controller 20 through a flow sensor (not shown in FIG. 1). The regular irrigation flow line 10'b is configured to be connectable with the irrigation line 50c of the medical device. This type of connection is well known in the art.

The low flow irrigation assembly includes a low flow irrigation container or storage device 10, a low flow irrigation pump and valve block 10a, a flow sensor 10c, and a low flow irrigation line 10b. As similarly described for the regular irrigation assembly, the low flow irrigation container 10 is used to store or hold an irrigation fluid. The low flow irrigation fluid may also be saline. The low flow irrigation pump and valve block 10a includes a fluid pump and at least a valve for controlling the flow of the low flow irrigation fluid. The low flow irrigation pump is used to transport the irrigation fluid from the irrigation container 10 to the medical device. The low flow irrigation pump and the valve block 10a may be built into one whole piece. However, it is preferable that they are physically separable. The fluid pump may be a peristaltic pump or other types of pumps. The pump and valve block 10a may comprise one or more valves so long as it is configured to be capable of moderating or controlling the flow rate, pressure, and/or volume of the regular irrigation assembly line. The valve may be a pinch valve or other types of valves. The flow rate, pressure, and volume are configured to be feedback monitored and controlled in a closed-loop manner by the logic controller 20 through the flow sensor 10c. The low flow irrigation flow line 10b is configured to be connectable with the irrigation line 50c of the medical device. Again, this type of connection is well known in the art.

The blade assembly 50a is in electrical communication with the RF generator 30 through the cable 50d. It may also be through other means such as wireless connection known in the art. The blade assembly 50a may be a monopolar surgical blade. It may also be a bipolar surgical blade. The design or selection of monopolar blade or bipolar blade is well known in the art.

The feature sensor 50b may include a plurality of different feature sensors or indicators that are in communication with the logic controller 20. Once the logic controller 20 receives data from these sensors, it will then compare them with the pre-established values or use look-up table, and subsequently make adjustments and/or controls accordingly.

The RF generator 30 is the type well known in the art. It may be manually turned on or off by a footswitch or push button 40 or automatically controlled by the logic controller 20. The push button 40 may also be configured to be disposed on the handpiece 50 using known techniques in the art.

The logic controller or processor 20 may be a microprocessor, an application specific integrated circuit (ASIC) state machine, a gate array, a controller, and the like. The logic controller is configured to be in communications with the regular irrigation pump and valve block 10'a, the low flow irrigation pump and valve block 10a, the low flow sensor 10c, the feature sensor 50b, and the RF generator 30. The logic controller may be configured to monitor and control the flow rate, pressure, and volume of the regular irrigation line through the regular pump and valve block 10'a. The logic controller may be configured to feedback monitor and control the flow rate, pressure, and volume of the low flow irrigation line in response to the input of the feature sensor 50b such as a temperature sensor. The logic controller may also be configured to monitor or control the temperature at the surgical blade of the medical device through the temperature sensor.

Figure 2:
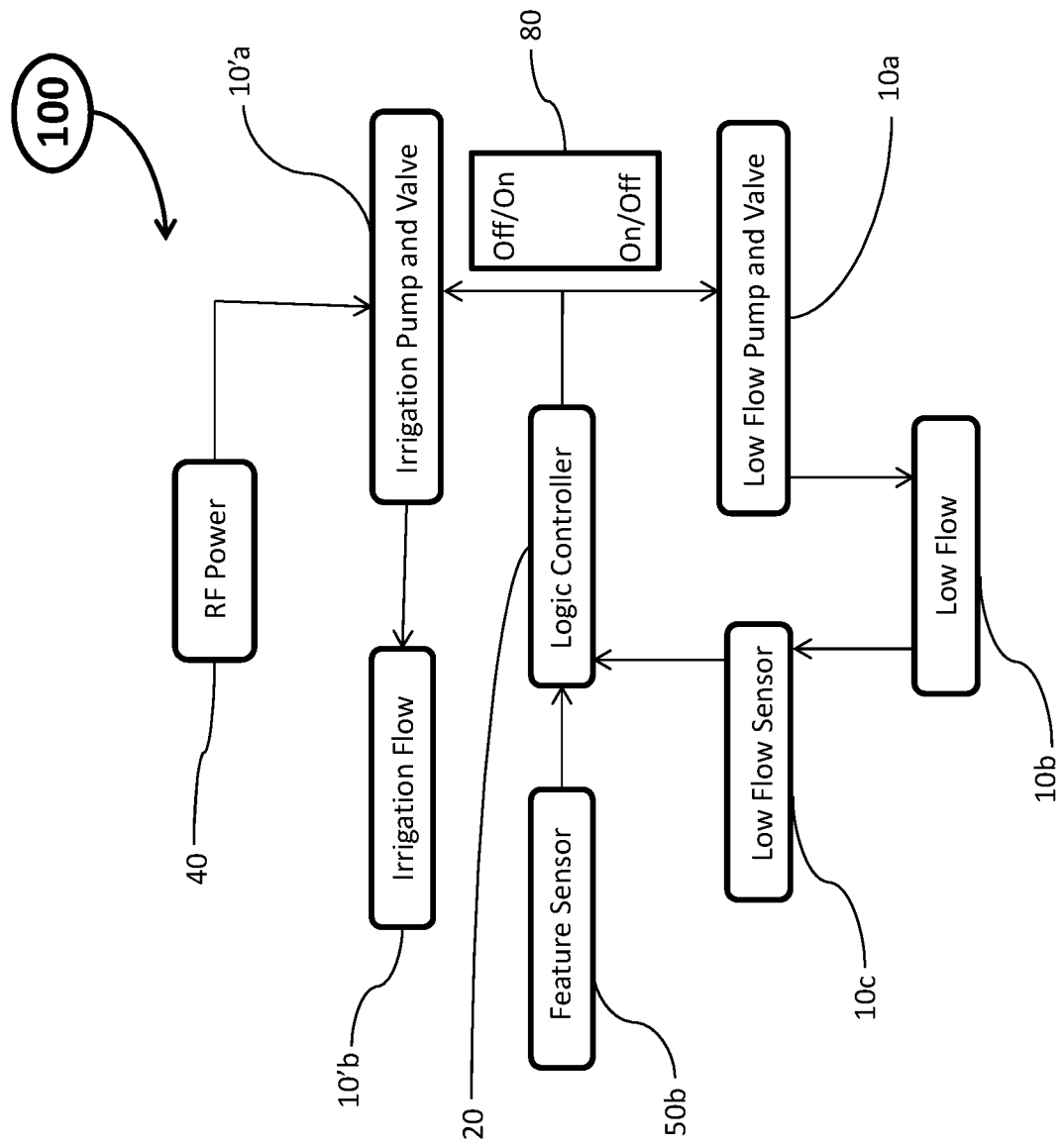
FIG. 2 is an operational and functional flowchart of the electrosurgical system as described in FIG. 1.

FIG. 2 is a simplified flow chart showing a method of monitoring and/or controlling a medical system 100 in accordance with FIG. 1. Initially, the RF power is off, and all the other components of the medical system are also power off. All the necessary connections are properly connected and secured. The surgical blade of the medical device is properly positioned at the treatment site. When the regular pump and the valve block 10'a is off, both the pump power is off and the valve closed. Consequently, there is no regular irrigation fluid flowing. Similarly, when the low flow pump and valve block 10a is off, the pump power is off and the valve closed. The whole system is in its off status. When the RF generator 40 is turned on by the footswitch or push button 40, the medical device may be subsequently turned on once the surgical blade 50a of the medical device is placed at its proper position ready to perform an electrosurgery. Once the electrosurgery is initiated, the regular pump and valve block 10'a starts transporting an irrigation fluid such as saline to the surgical blade 50a. The low flow irrigation pump and valve 10a still remains off. When the logic controller receives an input from the feature sensor 50b that indicates the received value is beyond or below certain value, the logic controller will turn off the regular pump and valve block 10'a, and concurrently turn on the low flow irrigation pump and valve 10a. The low flow irrigation rate and volume can be feedback controlled through the low flow irrigation flow sensor 10c. For example, the feature sensor 50b may be a temperature sensor, an electrical current indicator or recorder, an electrical current indicator or recorder, or a bioimpedance indicator or recorder. All the information from the feature sensor is sent to the logic controller and recorded therein. It may also be possible or even desirable that the regular irrigation pump and valve 10'a and the low flow irrigation pump and valve 10a may be manually turned on or off at any time when this has to be the case. The on/off of the regular pump and valve 10'a and the on/off the low flow irrigation pump and valve 10a (as shown at 80 of FIG. 3) may preferably be alternating. That is one is on, the other is off, and vice versa. However, it may be also configured to let both on at the same time if needed. The above irrigation cycles may be repeated many times as needed until the electrosurgery is completed.

Figure 3:
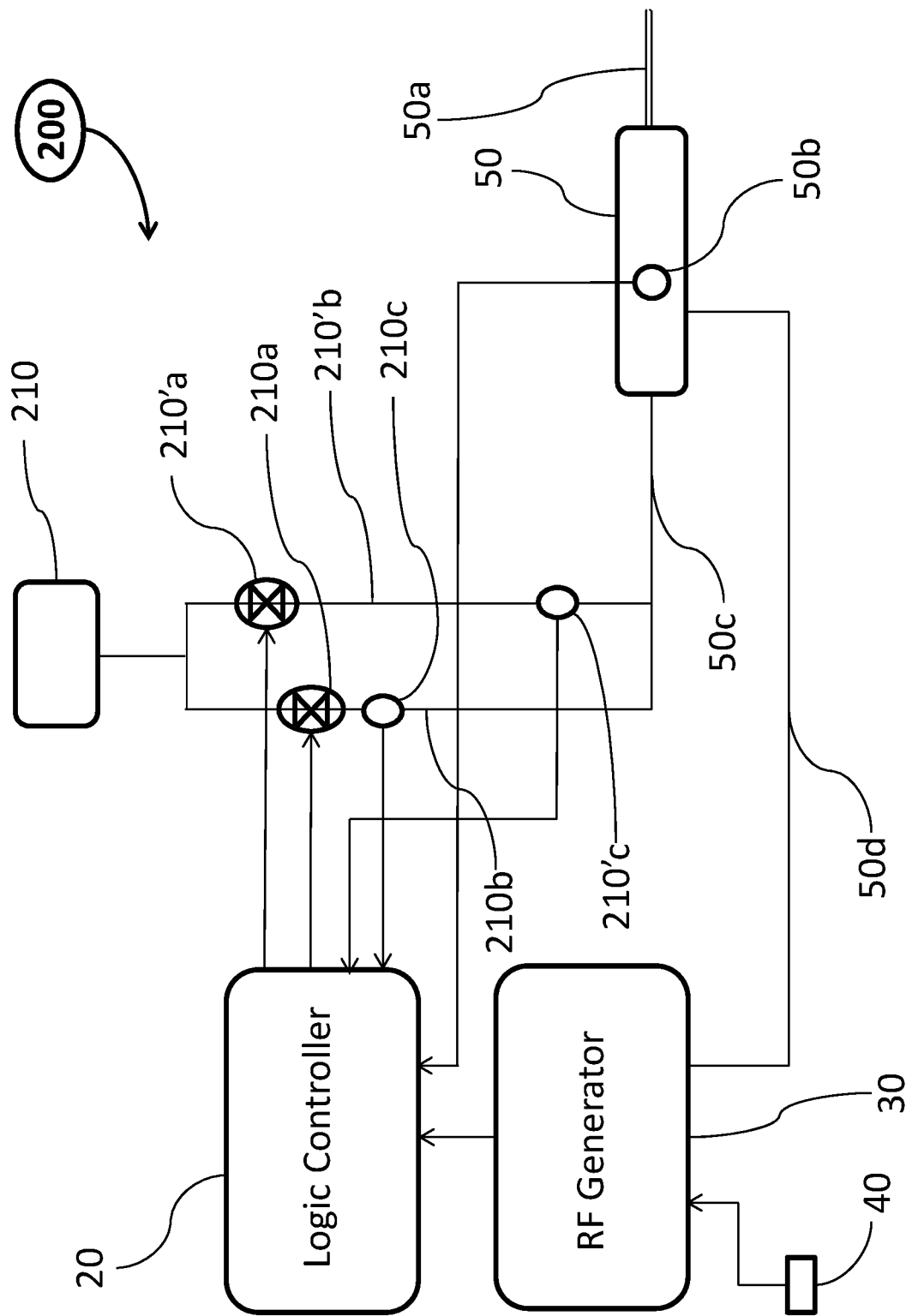
FIG. 3 is a block diagram of an electrosurgical system in accordance with another aspect of the present disclosure.

FIG. 3 is a block diagram in accordance with another aspect of the present disclosure. Similar to the medical system 100 as described with respect to FIG. 1, the medical system 200 of FIG. 3 includes a medical device, a regular irrigation assembly, a low flow irrigation assembly, a logic controller 20, and a RF generator 30. The description of the medical system 100 similarly applies to the description of the medical system 200 except the following two major differences. First, the regular irrigation container and the low flow irrigation contained are merged into one irrigation container 210. The other difference is that the regular irrigation assembly includes a regular irrigation flow sensor 210'c. The flow sensor 210'c is employed to send the flow related information to the logic controller 20 so that the logic controller can automatically monitor and control the flow rate and volume of the regular irrigation line in response to the input of the feature sensor 50b in addition to the low flow irrigation line. One of the reasons for adding this sensor is to better respond to broad and quick irrigation flow requirements.

Figure 4:
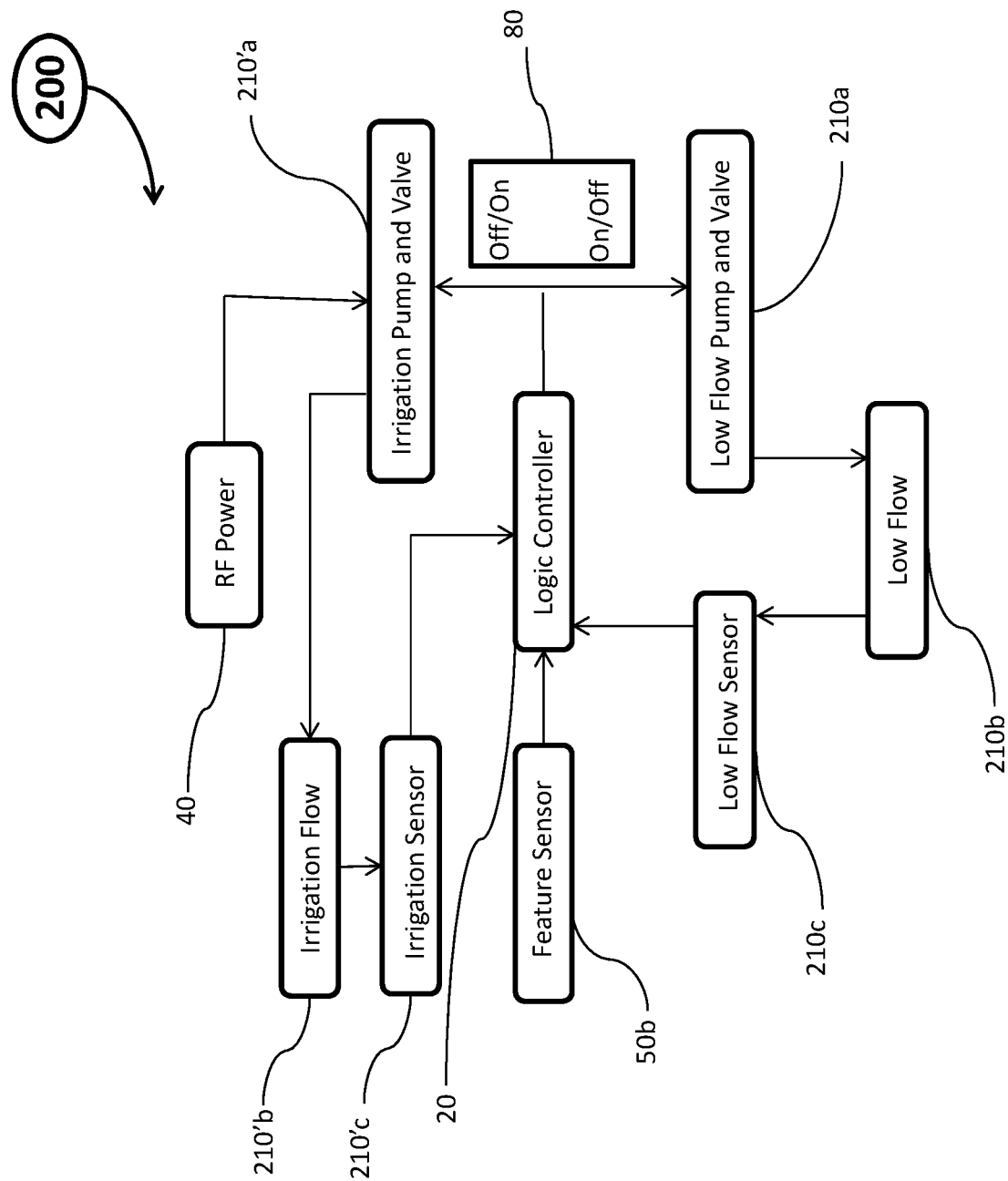
FIG. 4 is an operational and functional flowchart of the electrosurgical system as described in FIG. 3.

FIG. 4 is a simplified flow chart showing a method of monitoring and/or controlling a medical system 200 in accordance with FIG. 3. The method is similar to what was described with respect to FIG. 2. The significant difference is an addition of a flow sensor 210'c to the regular irrigation assembly in connection with the merging of the two fluid containers in FIG. 1. The flow sensor 210'c is configured to send information to the logic controller 20 for processing. The processed information will then be used for feedback control of the regular irrigation flow.

Figure 5:
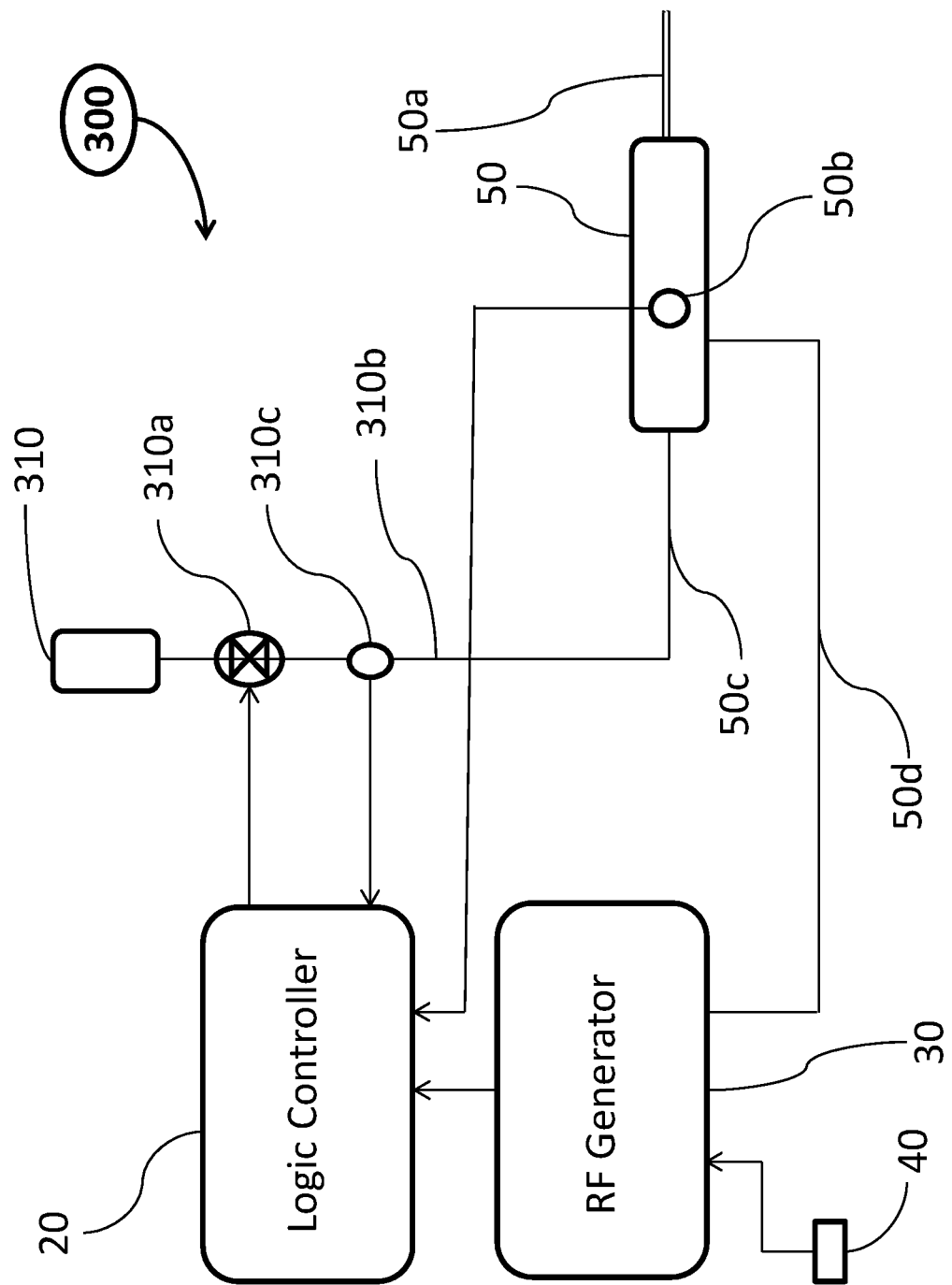
FIG. 5 is a block diagram of an electrosurgical system in accordance with yet another aspect of the present disclosure.

FIG. 5 is a block diagram in accordance with another aspect of the present disclosure. Different from a medical system 100 or 200, the medical system 300 of FIG. 5 includes a combined irrigation assembly. The combined irrigation assembly includes an irrigation container 310, an irrigation pump and valve 310a, a combined irrigation line 310b, and a combined irrigation flow sensor 310c. The functions of these components are similar to their respective components as descried with respect to FIG. 1 or FIG. 3. The medical system 300 presents a simpler configuration in comparison with a medical system 100 or 200, and yet accomplishes identical or similar functions as desired. However, it may put stricter requirements of compatibility of the system components. Regardless, the medical system 100 or 200 should always serve the need.

Figure 6:
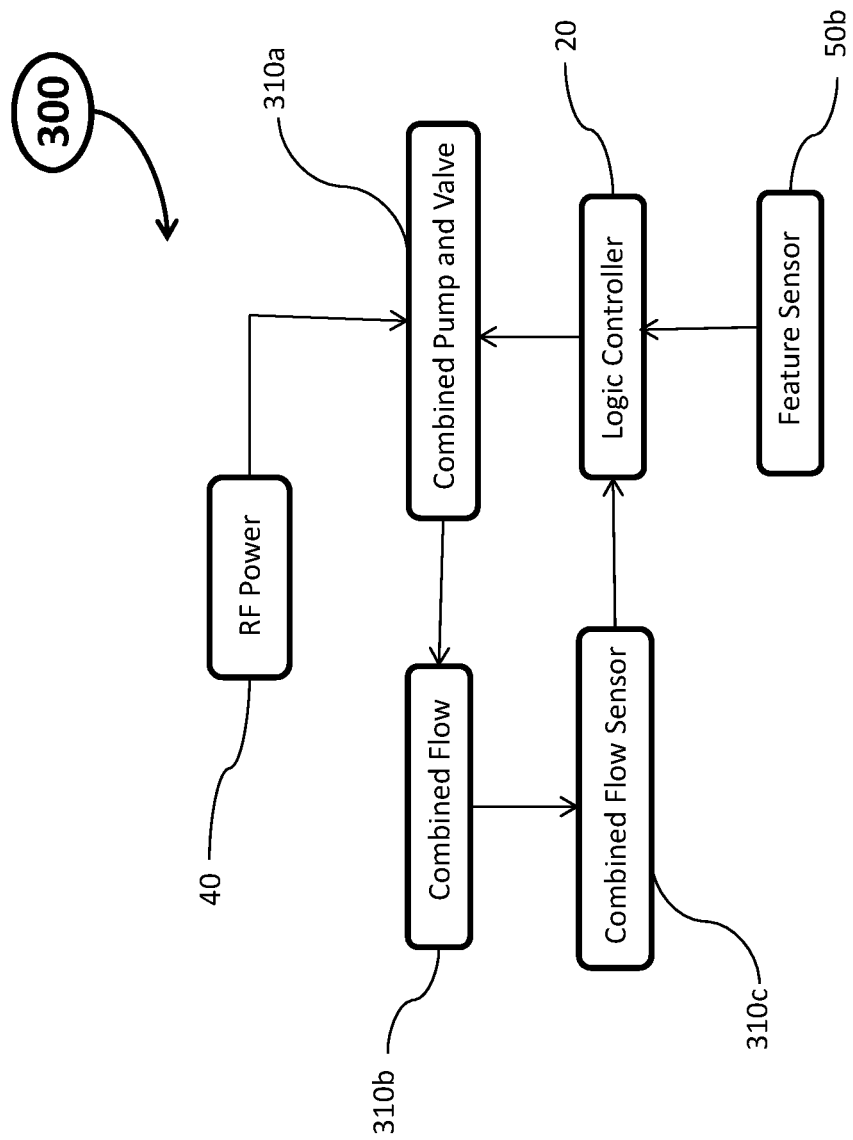
FIG. 6 is an operational and functional flowchart of the electrosurgical system as described in FIG. 5.

FIG. 6 is a simplified flow chart showing a method of monitoring and/or controlling a medical system 300 in accordance with FIG. 5. The chart may appear to be simpler in comparison with a method as described for the medical system 100 or 200. However, as stated above, it may put stricter requirements of compatibility of the system components. Still though, this should be all within the knowledge of an ordinary skill in the art.

Figure 7:
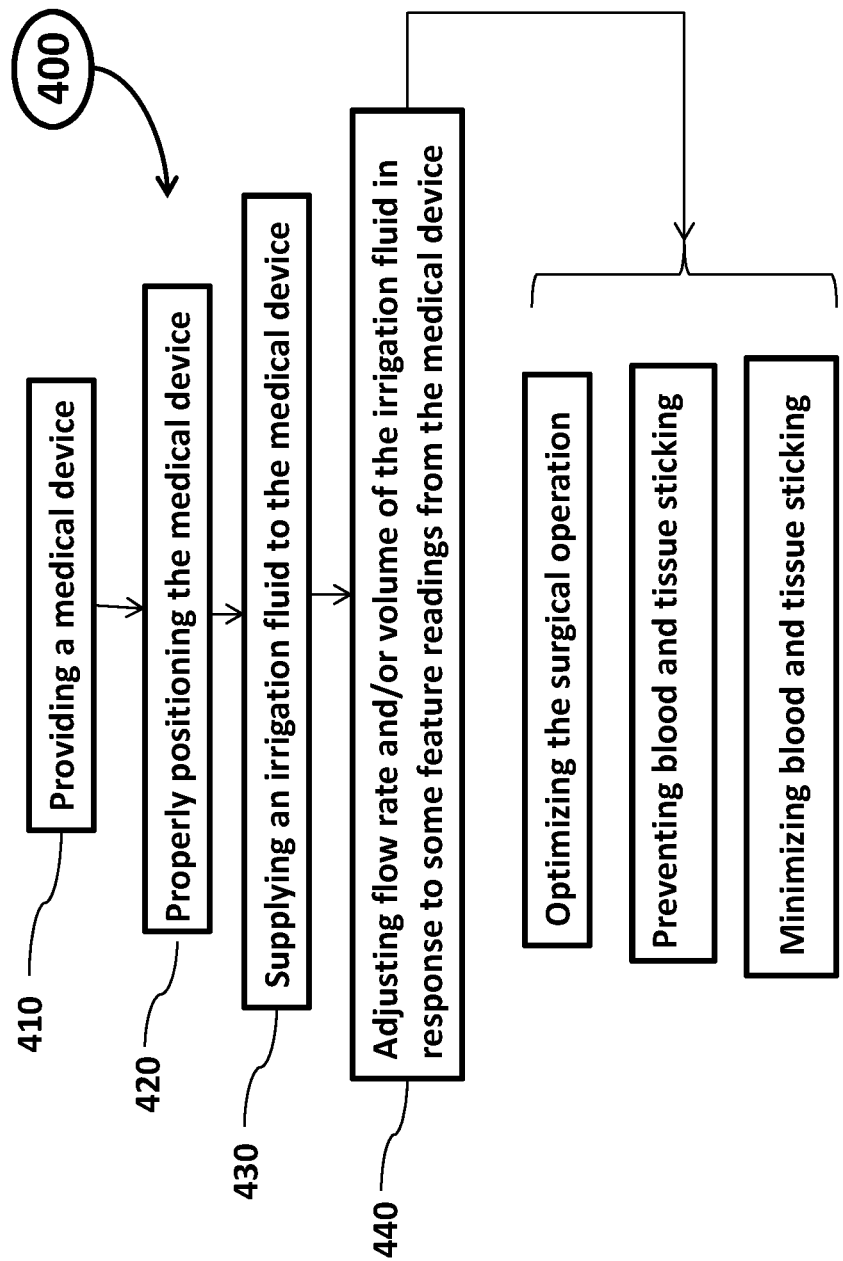
FIG. 7 is a flowchart of a method of operating an electrosurgical device in accordance with one aspect of the present disclosure.

FIG. 7 shows a method of optimizing or improving a surgical operation of an electrosurgical device, or minimizing or even preventing formation of blood and tissue sticking on a surgical blade of the electrosurgical device. The method 400 comprises step 410 which provides a medical device having a surgical blade and an irrigation line. The associated step also includes providing an irrigation container storing/holding an irrigation fluid such as saline. The associated step also includes providing necessary accessories connecting the irrigation container to the irrigation line of the medical device. The associated step also includes providing a RF generator that can provide RF energy to the medical device. The method 400 also comprises step 420 of positioning the provided medical device properly at a treatment site. This may be accomplished through the guidance of an endoscope or other means such as ultrasonic guidance. It may also be accomplished through a guidewire, access sheath and/or balloon sheath. The method 400 also includes step 430 of supplying an irrigation fluid to the medical device. Once the medical device is properly positioned, and the medical device is initiated to perform an operation, the step 430 starts. The operator observes the progress of the operation through an endoscope or other means. Once the operator finds any sign of tissue and/or blood sticking on the surgical blade of the medical device, the operator makes adjustments of the flow rate of the irrigation fluid (step 440). The operator may make adjustments of the flow rate to about 0.1 to 0.25 ml per second. The operator may also make adjustments once he finds an increased fog accumulation or temperature rise around the surgical blade of the medical device. The operator may make adjustments of the temperature at the surgical blade to be about 80 to 99° C. degree. The operator is thus able to optimize or improve the outcome of a surgical operation, and may minimize and even prevent blood and tissue sticking or accumulation on the surgical blade of the medical device.

It is understood that the above description is intended to be illustrative and not restrictive. Many embodiments as well as many applications besides the examples provided will be apparent to those of skill in the art upon reading the above description. The scope of the teachings should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. The omission in the following claims of any aspect of subject matter that is disclosed herein is not a disclaimer of such subject matter, nor should it be regarded that the inventors did not consider such subject matter to be part of the disclosed inventive subject matter.

We claim:

1. A medical system comprising:
   a medical device having a surgical electrode and an irrigation line;
   a regular irrigation assembly configured to be in fluid communication with the irrigation line of the medical device, where the regular irrigation assembly comprises a first device configured to control irrigation flow with the irrigation line;
   a low flow irrigation assembly configured to be in fluid communication with the irrigation line of the medical device, where the low flow irrigation assembly comprises a second device configured to control irrigation flow with the irrigation line;
   a logical controller; and
   a feature sensor,
   wherein the feature sensor is a temperature sensor provided on the medical device and operable to sense temperature at a treatment site,
   wherein the regular irrigation assembly includes a regular flow sensor configured to be in communication with the logical controller,
   wherein the low flow irrigation assembly includes a low flow sensor configured to be in communication with the logical controller, and
   wherein the logical controller is configured to control an irrigation flow rate of a first and second selected irrigation flow through the irrigation line of the medical device in response to an input of the temperature sensor such that:
      the regular irrigation assembly is configured to provide the first selected irrigation flow rate when the second device of the low flow irrigation assembly is off; and
      the low flow irrigation assembly is configured to provide the second selected irrigation flow rate when the first device of the regular irrigation assembly is off, wherein the second selected irrigation flow rate is different than the first selected irrigation flow rate.

2. The medical system of claim 1, wherein the low flow sensor is configured to be feedback controlled by the logical controller in response to the input of the feature sensor.

3. The medical system of claim 1, wherein the medical device is a monopolar electrosurgical device.

4. The medical system of claim 1, wherein the medical device is a bipolar electrosurgical device.

5. The medical system of claim 1,
   wherein the first device comprises a first valve block, the first valve block configured to turn on or off the regular irrigation assembly for inputting the selected irrigation flow, and
   wherein the second device comprises a second valve block, the second valve block configured to turn on or off the low flow irrigation assembly for inputting the selected irrigation flow.

6. The medical system of claim 1, wherein the logical controller is configured to control the irrigation flow rate of the selected irrigation flow through the irrigation line of the medical device in response to the input of the temperature sensor to control the temperature of the medical device.

7. The medical system of claim 6, wherein the logical controller is configured to control the temperature at a surgical blade of the medical device through the temperature sensor.

8. The medical device of claim 7, wherein the temperature sensor is disposed at a tip of the surgical blade.

9. The medical device of claim 1, wherein the temperature sensor comprises an IR temperature sensor.

10. The medical device of claim 1, wherein the temperature sensor comprises a thermistor.

11. The medical system of claim 1, wherein the temperature sensor comprises a thermocouple.

12. The medical system of claim 1, wherein the temperature sensor is disposed at a distal end or tip of the medical device.

13. A medical system comprising:
   a medical device having a surgical electrode and an irrigation line;
   a regular irrigation assembly configured to be in fluid communication with the irrigation line of the medical device, where the regular irrigation assembly comprises a first valve block configured to turn on or off the regular irrigation assembly;
   a low flow irrigation assembly configured to be in fluid communication with the irrigation line of the medical device, where the low flow irrigation assembly comprises a second valve block configured to turn on or off the low flow irrigation assembly;
   a logical controller; and
   a temperature sensor provided on the medical device and operable to sense temperature at a treatment site;
   wherein the regular irrigation assembly includes a regular flow sensor configured to be in communication with the logical controller,
   wherein the low flow irrigation assembly includes a low flow sensor configured to be in communication with the logical controller,
   and
   wherein the logical controller is configured to automatically control an alternating irrigation flow rate of a first and second selected irrigation flow through the irrigation line of the medical device in response to an input of the temperature sensor such that:
      the regular irrigation assembly is configured to provide the first selected irrigation flow rate when the second valve block of the low flow irrigation assembly is off; and
      the low flow irrigation assembly is configured to alternatively provide the second selected irrigation flow rate when the first valve block of the regular irrigation assembly is off.

14. A medical system comprising:
   a medical device having a surgical electrode and an irrigation line;
   a regular irrigation assembly configured to be in fluid communication with the irrigation line of the medical device, where the regular irrigation assembly comprises a first device configured to control irrigation flow with the irrigation line;
   a low flow irrigation assembly configured to be in fluid communication with the irrigation line of the medical device, where the low flow irrigation assembly comprises a second device configured to control irrigation flow with the irrigation line;
   a logical controller; and
   a feature sensor,
   wherein the feature sensor is a temperature sensor provided on the medical device and operable to sense temperature at a treatment site,
   wherein the regular irrigation assembly includes a regular flow sensor configured to be in communication with the logical controller,
   wherein the low flow irrigation assembly includes a low flow sensor configured to be in communication with the logical controller, and wherein the logical controller is configured to control at least one of an irrigation flow rate, an irrigation flow volume, or an irrigation flow pressure of a first and second selected irrigation flow through the irrigation line of the medical device in response to an input of the temperature sensor such that:

the regular irrigation assembly is configured to provide the at least one of the first selected irrigation flow rate, the first selected irrigation flow volume, or the first selected irrigation flow pressure when the second device of the low flow irrigation assembly is off; and the low flow irrigation assembly is configured to provide the at least one of the second selected irrigation flow rate, the second selected irrigation flow volume, or the second selected irrigation flow pressure when the first device of the regular irrigation assembly is off, wherein the at least one of the second selected irrigation flow rate, the second selected irrigation flow volume, or the second selected irrigation flow pressure is different than the at least one of the first selected irrigation flow rate, the first selected irrigation flow volume, or the first selected irrigation flow pressure.

* * * * *